United States Patent [19]
Hurbis

[11] Patent Number: 6,106,541
[45] Date of Patent: Aug. 22, 2000

[54] SURGICALLY IMPLANTABLE NASAL DILATOR

[76] Inventor: Charles G. Hurbis, 1880 Brookfield Dr., Saline, Mich. 48176

[21] Appl. No.: 09/072,624

[22] Filed: May 5, 1998

Related U.S. Application Data

[60] Provisional application No. 60/046,907, May 16, 1997.
[51] Int. Cl.[7] .................................................. A61M 29/00
[52] U.S. Cl. ......................... 606/199; 606/191; 606/198
[58] Field of Search ................................. 606/190, 191, 606/196, 198, 199, 204.45; 128/200.24; 623/10; 604/11; 602/46

[56] References Cited

U.S. PATENT DOCUMENTS

| | | | |
|---|---|---|---|
| 4,414,977 | 11/1983 | Rezakhany | 606/199 |
| 5,336,163 | 8/1994 | Demane et al. | 602/46 |
| 5,533,503 | 7/1996 | Doubek et al. | 128/200.24 |
| 5,546,929 | 8/1996 | Muchin | 128/200.24 |
| 5,589,176 | 12/1996 | Seare, Jr. | 424/400 |
| 5,611,333 | 3/1997 | Johnson | 128/200.24 |

*Primary Examiner*—Wynn Wood Coggins
*Assistant Examiner*—Jennifer Maynard
*Attorney, Agent, or Firm*—Harness, Dickey & Pierce, P.L.C.

[57] ABSTRACT

A surgically implantable nasal dilator for implanting within the nasal tissues of a user having an internal skeleton structure of inverted V-shape capable of being implanted within the nasal tissues of a user and imparting an oppositely directed opening force on the wall tissues of the nose of the user, and an external sheath, formed from a biocompatible material, encasing the internal skeleton structure.

1 Claim, 1 Drawing Sheet

SURGICALLY IMPLANTABLE NASAL DILATOR

This application claims benefit of provisional application 60/046,907, filed May 16, 1997.

BACKGROUND AND SUMMARY OF THE INVENTION

This invention is related to nasal dilators and particularly to a surgically implantable nasal dilator, having an internal generally open "V"-shaped skeleton structure encased within an external biocompatible covering material, which urges the wall tissues of the nasal passageways outward, thereby opening the nasal passageways and reducing the likelihood of nasal passageway blockage during inhalation.

Nasal valve dysfunction is an extremely prevalent medical condition, particularly in the geriatric population. To compensate for this condition, external nasal dilators, such as devices sold under the "Breathe Right" trademark by CNS, Inc., 1250Park Road, Chanhassen, Minn. 55317, have begun to receive widespread commercial acceptance. Devices of this type are shown in U.S. Pat. No. 5,533,449. Breathe Right™ external nasal dilators have been marketed to the geriatric population, as well as to athletes and patients with sleep apnea or snoring. Other types of external nasal dilators are known, such as those described in U.S. Pat. No. Re. 35,408.

A significant disadvantage of external nasal dilators is that they need to be affixed externally each time they are used. Because they are attached to the exterior of the face, typically by an adhesive, they are quite noticeable cosmetically and are normally not reusable.

Various devices which are intended to be manually inserted into the nasal cavities of the user to open up the nasal passageways are also known. These devices are commonly known as nostril expanders and are described, for instance, in U.S. Pat. Nos. 851,048 and 1,597,331. These devices are intended to inserted by the user prior to each use and removed by the user at the end of each use. These types of nostril expanders are, however, quite uncomfortable to wear. Because they are typically made from a material that is not adequately biocompatible, they can cause nasal tissue irritation and itching. Due to the physical discomfort caused by wearing these types of devices, they cannot typically be left inserted for long periods of time, such as while the user sleeps.

An improved nasal dilator is therefore desirable that would provide permanent relief of nasal valvular dysfunction and would not require affixation each time it is used. It is also desirable to provide an improved nasal dilator that is not visible during use. It is further desirable to provide an improved nasal dilator that may be permanently implanted and that will not cause physical discomfort to the user.

In accordance with the present invention, an surgically implantable nasal dilator is disclosed having an internal open "V"-shaped skeleton structure encased within an external biocompatible sheath material. The surgically implantable nasal dilator is quite small and is easily implantable into the nasal tissues of a user through a simple 0.5 centimeter central nasal incision.

The center portion of the surgically implantable nasal dilator (i.e. the middle portion of the "V") may be positioned external to the upper lateral cartilages of the user. The opposing ends of the device (i.e. the opposed ends of the "V") may be positioned superior to the lower lateral cartilages of the user. The arms of the device (i.e. the portions between the central portion and the opposing ends of the device) are typically compressed toward each other during implantation and when released, these arms produce a force which urges the wall tissues of the nasal passageways outwardly, thereby opening the nasal passageways of the user and reducing the likelihood of nasal passageway blockage during inhalation.

The surgically implantable nasal dilator is fabricated from two types of materials that have distinctly different required material properties. The internal skeleton structure of the surgically implantable nasal dilator is a structural element designed to produce the outward opening force on the wall tissues of the user. The internal skeleton structure must therefore be constructed of a structural material capable of producing this outward opening force. The internal skeleton structure is encased within an external sheathing material which is intended to reduce the likelihood of tissue irritation or foreign body rejection problems caused by the implanted surgically implantable nasal dilator. The external sheathing material must therefore be biocompatible with human facial tissue. The performance characteristics of these materials and a description of suitable materials are discussed in more detail below.

After being implanted, the surgically implantable nasal dilator may effectively and permanently solve a patent's nasal valvular dysfunction. The device would not be visible and would be virtually undetectable after it is implanted. Increased airway performance and decreased nasal passageway blockage would be enjoyed around the clock instead of those relatively short periods in which an external nasal dilator is worn. Once implanted, the surgically implantable nasal dilator can be comfortably worn for a lifetime and can provide significant reductions in nasal airflow problems.

Further objects, features and advantages of the invention will become apparent from a consideration of the following description and the appended claims when taken in connection with the accompanying drawings.

DETAILED DESCRIPTION OF THE PREFERRED EMBODIMENT

Figure 1:
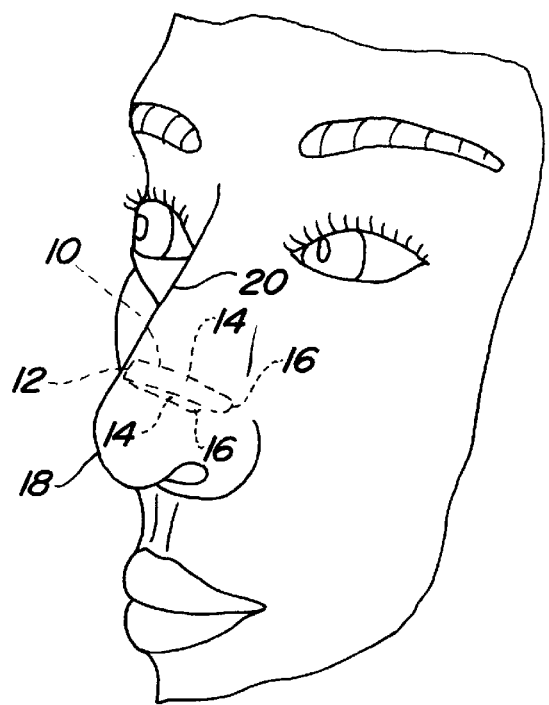
FIG. 1 is a partial perspective view of the face of a user, showing in phantom an implanted surgically implantable nasal dilator in accordance with this invention.

A surgically implantable nasal dilator is shown in phantom in an implanted condition in FIG. 1 and is generally designated by reference number 10. Surgically implantable nasal dilator 10 consists of a generally inverted open "V"-shaped structure which is surgically implanted subcutaneously within the nasal tissues of a user. The surgically implantable nasal dilator 10 has a center portion 12 and a pair of arm portions 14 that terminate in end portions 16. The center portion 12 (i.e. the middle portion of the "V") is positioned along the centerline of the nose approximately halfway between the tip of the nose 18 and the outermost portion of the nasal bone 20.

The arm portions 14 of the surgically implantable nasal dilator 10 are implanted into the nasal tissues in such a way that they produce outward opening forces on the wall tissues of the nasal passageways, particularly near the end portions 16, thereby opening the nasal passageways and reducing the likelihood of nasal passageway blockage during inhalation. To produce this result, the arm portions 14 of the surgically implantable nasal dilator 10 may have to be compressed toward each other during the implantation process (from their non-implanted unflexed positions) or the wall tissues of the nasal passageways may have to be urged outwardly (from their normal resting positions) during the implantation process. Both of these conditions may occur simultaneously during the implantation process. When the implantation is complete, due to their relatively compressed position, the arm portions 14 of the surgically implantable nasal dilator 10 will urge the wall tissues of the nasal passageways outwardly.

Figure 2:
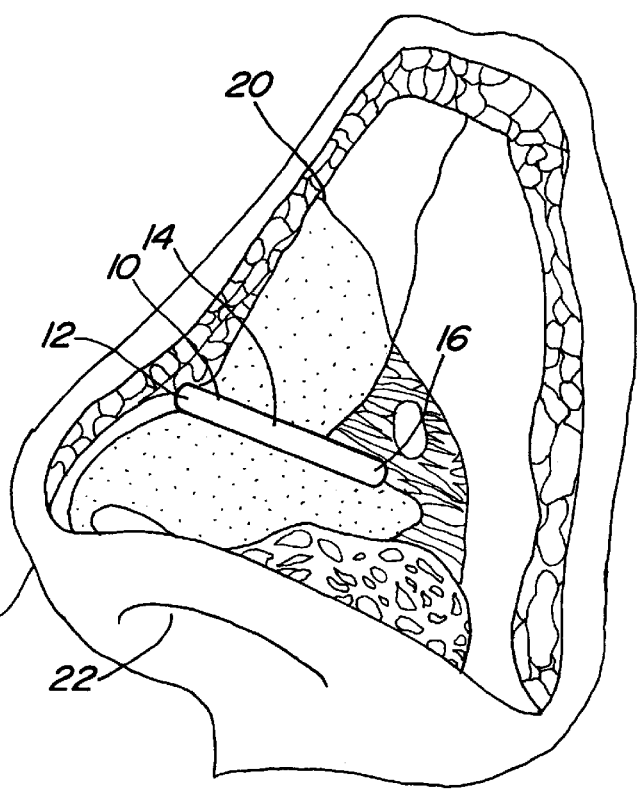
FIG. 2 is a cut-away view through the face of the user from FIG. 1, particularly showing the position of the implanted surgically implantable nasal dilator with respect to the nasal structures of the user.

FIG. 2 shows a cut-away view through the face of the user from FIG. 1, and more particularly shows the position of the implanted surgically implantable nasal dilator 10 which respect to the nasal structures of the user. The center portion 12 is implanted external to the upper lateral cartilages of the user. The center portion 12 is positioned along the centerline of the nose approximately halfway between the tip of the nose 18 and the outermost portion of the nasal bone 20. The arm portions 14 are positioned superior to the lower lateral cartilages of the user and exert an outward force on the fleshy walls of opposing sides of the nose. Only one arm portion 14 is visible from this view. The other arm portion 14 is hidden directly behind the visible arm portion from this perspective. The arm portions 14 are oriented approximately parallel to the respective nostril openings 22 of the user.

Figure 3:
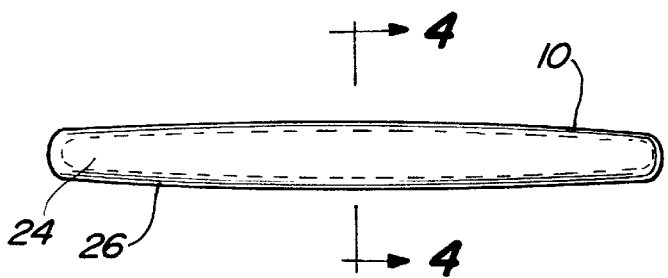
FIG. 3 is an enlarged top down view of the surgically implantable nasal dilator.

FIG. 3 shows an enlarged top down view of the surgically implantable nasal dilator 10 in the unflexed, non-implanted position. Surgically implantable nasal dilator 10 consists of an internal skeleton structure 24, shown in phantom, and an external encasing sheath 26.

The internal skeleton structure 24 is fabricated from a material that must continue to maintain an outward opening force for long periods of time, with little or no diminution or loss of force transmission characteristics. The material must be capable of repetitively flexing without failure. The material must also be tough enough to avoid being damaged under any type of contact or trauma the user's face could reasonably be expected to be subjected to during the user's lifetime. The material must also be relatively benign biologically, so that a severe adverse reaction would not be caused in the unlikely event that the external encasing sheath 26 of the surgically implantable nasal dilator 10 is somehow dislodged from the internal skeleton structure 24 and the internal skeleton structure material comes into direct contact with the users nasal tissue. The internal skeleton structure 24 of the surgically implantable nasal dilator 10 could consist of virtually any material that has these material properties, although a springy stainless steel or nylon material may be preferable.

The dimensions and shape of the internal skeleton structure 24 would typically be customized or selected from a wide variety of alternative sizes to assure that the surgically implantable nasal dilator 10 precisely fits the dimensions of the nasal tissues of the user. The length, width and angle formed between the arm portions 14 of the surgically implantable nasal dilator 10 could be customized to provide the desired outward force and force distribution on the nasal wall tissues of the user.

The internal skeleton structure 24 will typically be a relatively smooth rounded structure, with no sharp or rough edges that could irritate or traumatize the nasal tissues of the user in the unlikely event that the internal skeleton structure became disassociated from the external encasing sheath 26.

The external encasing sheath 26 must consist of a material that is biocompatible when implanted into the face. Suitable materials include expanded polytetrafluroethylene (PTFE) materials sold under the trade name Goretex® by W.L. Gore & Associates, Inc., Flagstaff, Ariz. 86003. Goretex® has been used for surgical purposes for many years, mostly in the form of vascular grafts and has recently been used for many cosmetic surgical applications. Extensive use of Goretex® implants in the face has been very successful, with few complications. Goretex® is one of the few substances that are biocompatible enough to be implantable in the face. The use of Goretex® material as the external encasing sheath 26 in the surgically implantable nasal dilator 10 is simply a different application of a time tested material that has a very safe track record.

Figure 4:
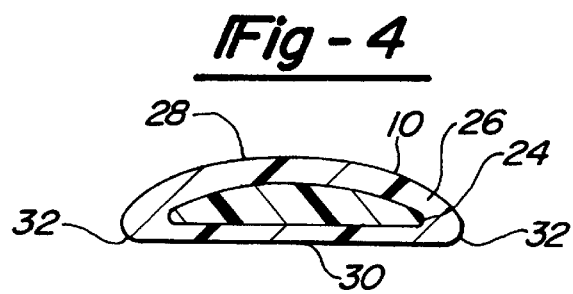
FIG. 4 is an enlarged cross-sectional view of the surgically implantable nasal dilator, taken along line 4—4 in FIG. 3, showing in greater detail the internal structure of the surgically implantable nasal dilator.

FIG. 4 shows a cross-sectional view of the surgically implantable nasal dilator 10 taken along line 4—4 in FIG. 3. The top 28 of the surgically implantable nasal dilator 10, which will be outwardly facing when the dilator has been implanted, has a generally crowned shape. The bottom 30 of the surgically implantable nasal dilator 10, which will be inwardly facing when the dilator has been implanted, has a generally flat shape. The edges 32 of the surgically implantable nasal dilator 10 are rounded.

Other embodiments of the surgically implantable nasal dilator 10 are possible, including embodiments in which the internal skeleton structure and the external encasing sheath are formed from the same material. The surgically implantable nasal dilator 10 may also be effectively implanted in various other positions and orientations other than those shown in FIGS. 1 and 2.

It is to be understood that the invention is not limited to the exact construction illustrated and described above, but that various changes and modifications may be made without departing from the spirit and scope of the invention defined as:

A surgically implantable nasal dilator for implanting within the nasal tissues of a user having:

an internal skeleton structure capable of being implanted within the nasal tissues of a user and imparting an opening force on the wall tissues of the nose of the user, and an external sheath, formed from a biocompatible material, encasing the internal skeleton structure.

What is claimed is:

1. A surgically implantable dilator for use in a human nose adjacent the cartilaginous tip and nasal bones, said structure implantable within the nasal tissues in the nose for maintaining the nasal passageways therein open and reducing the likelihood of blockage of the passageways during inhalation, said dilator comprising:

an internal skeleton structure capable of being flexed to an inverted V-shape having a center portion and downwardly diverging arms, said structure being implanted within the nasal tissues in said nose so that said center portion of said skeleton structure is implanted external to the upper lateral cartilages along the centerline of said nose at a point generally halfway between the tip of the nose and the nasal bone, said arms extending downwardly and being biased in directions away from each other at positions superior to the lateral cartilages of the nose into engagement with the side walls of opposing sides of the nose so that said arms can impart opening forces on said side walls of the nose to thereby allow for uninhibited air flow therethrough, and an external sheath formed from a material that is biocompatible for implantation in human facial tissue and encasing said internal skeleton structure, said sheath having a relatively flat bottom wall and a rounded upper wall and rounded edges.

* * * * *